United States Patent [19]

Afseth et al.

[11] Patent Number: 5,429,927
[45] Date of Patent: Jul. 4, 1995

[54] ANTIGEN/ANTI-ANTIGEN CLEAVAGE

[75] Inventors: John Afseth; Steiner Funderud, both of Oslo, Norway; Laurent Caignault, Choisy-au-Bac; Mohamad Mortada, Compi,ègne, both of France

[73] Assignee: Dynal AS, Oslo, Norway

[21] Appl. No.: 946,330

[22] PCT Filed: Apr. 9, 1991

[86] PCT No.: PCT/EP91/00671

§ 371 Date: Nov. 10, 1992

§ 102(e) Date: Nov. 10, 1992

[87] PCT Pub. No.: WO91/15766

PCT Pub. Date: Oct. 17, 1951

[30] Foreign Application Priority Data

Apr. 9, 1990 [GB] United Kingdom ............... 9007966

[51] Int. Cl.⁶ ................ G01N 33/543; G01N 33/553; G01N 33/569; C07K 17/00
[52] U.S. Cl. ........................................ 435/7.2; 435/2; 435/7.24; 435/239; 435/240.2; 435/243; 435/261; 435/975; 436/512; 436/518; 436/526; 530/391.1
[58] Field of Search ............... 435/2, 7.24, 174, 176, 435/177, 975, 965, 240.2, 239, 243, 261; 436/526, 528, 512, 518; 530/391.1, 863

[56] References Cited

U.S. PATENT DOCUMENTS

| | | | |
|---|---|---|---|
| 4,536,479 | 8/1985 | Vander-Mallie | 435/965 |
| 4,861,705 | 8/1989 | Margel | 435/2 |
| 5,081,030 | 1/1992 | Civin | 435/2 |

FOREIGN PATENT DOCUMENTS

| | | |
|---|---|---|
| 119629 | 9/1984 | European Pat. Off. |
| 170302 | 2/1986 | European Pat. Off. |
| 323829 | 7/1989 | European Pat. Off. |
| 88/02776 | 4/1988 | WIPO |
| WO91/09938 | 7/1991 | WIPO |

OTHER PUBLICATIONS

Thomas, et al., "Specific Binding and Release of Cells from Beads Using Cleavable Tetrameric Antibody Complexes", J. of Immunological Methods, 120 (1989) pp. 221–231.

Basch et al, 1983. Cell separation using positive immunoselective techniques. J. Immunol. Meth. 56: pp. 269–280.

Romain et al, 1984. Use of anti-Fab columns for the isolation of human lymphocyte populations. Meth. Enzymol. 108: pp. 148–153.

Kessler et al, 1987. Large-scale purification and characterization of CD-34 positive hematopoietic progenitor cells. Blood 70 (Suppl. 1): 321a.

Goding, 1983, *Monoclonal Antibodies: Principles and Practices.* Academic Press, London. pp. 7, 11–12.

Dynal, Apr. 1991. Detach a Bead product. Dynal, Inc. Great Neck, N.Y.

Rasmussen et al, 1992. A new method for detachment of Dynabeads from positively selected B lymphocytes. J. Immunolog. Meth. 146: 195–202.

Primary Examiner—David Saunders
Assistant Examiner—James L. Grun
Attorney, Agent, or Firm—Foley & Lardner

[57] ABSTRACT

The present invention provides a method of cleaving an antigen/anti-antigen or hapten/anti-hapten linkage joining two particles comprising reacting said linkage with a secondary antibody, or fragment thereof, binding to said anti-antigen or anti-hapten, and a kit for performing such a method. The method of the invention has particular utility in the separation of cells.

13 Claims, No Drawings

ANTIGEN/ANTI-ANTIGEN CLEAVAGE

The invention relates to a method of cleaving antigen/anti-antigen and hapten/anti-hapten linkages;

In biochemistry and related fields it is frequently desirable to link two chemical or biochemical entities, for example in isolation or purification or in the immobilisation of substances on solid supports. In particular it is often required to isolate cells by attaching them to substances assisting in their isolation and to isolate the cells subsequently in viable form.

Such linkage is often accomplished using affinity binding, that is by means of a pair of binding partners which are, for example, separately attached to the substances to be linked and which bind when brought into contact. Alternatively one of the binding partners may form a part of the entity requiring linkage, for example a molecule on a cell surface. A number of binding partner systems are known, for example antigen-antibody, enzyme-substrate, ligand-receptor interactions on cells and biotin-avidin binding. Antigen-antibody binding partners are however most frequently used in this regard, although the use of a hapten/anti-hapten binding pair has also recently been proposed.

Affinity binding systems are generally reversible, but it has been found, however, that particularly with antigen-antibody binding partners such linkages are difficult to reverse without destructive effects. Thus, whilst a linkage having a weak interaction strength (eg $Ka = 10^{-4} - 10^{-6} M^{-1}$) can be broken under mild conditions for example by competition with an analogue of the "ligand" binding partner, where the linkage is stronger (eg $Ka > 10^{-8} M^{-1}$), competitions kinetics do not suffice and more drastic conditions are necessary eg pH modification, salting out, in order to modify the conformation of the binding partner(s) and thereby reduce the interaction strength. For the cleavage method to be of use, the conformational changes induced during such a cleavage step must be reversible, and the binding partners should recover their functions upon return to the original conditions. Unfortunately, in the case of antigen/antibody binding, which must be of the order of at least $10^{-8} M^{-1}$ to be effective in allowing specific and rapid separation, whilst the antibody molecule can usually recover its native activity following such a cleavage treatment the antigen frequently is irreversibly altered and its native properties are lost. This is particularly a problem in the separation of cells or bacteria where it is important to maintain viability. Moreover, it is often desirable to be able to liberate the entities being linked in an unmodified native form, i.e. without any foreign substances remaining attached. This is particularly true in the case of cell isolation, where any foreign substances remaining attached to the surface of the liberated cells tend to interfere in cell reproduction and viability.

Cells are commonly linked, or bound, by employing antibodies which bind to antigens or haptens on the cell surface. As mentioned above antigen/antibody linkages are particularly difficult to reverse, and methods which cleave the antigen/antibody in such a manner that a part of the antibody remains attached are not particularly suited for use in cell isolation and separation procedures. Thus there exists a need for an improved method of cleaving antigen/anti-antigen or hapten/anti-hapten linkages with minimal destructive effect and in a manner which leaves the antigen or hapten and anti-antigen or anti-hapten binding partners intact.

We have now found that the linkages in antigen/anti-antigen or hapten/anti-hapten linkage systems may readily be broken by reacting the linkage system with an antibody directed against the anti-antigen or anti-hapten binding partner, or with a fragment thereof which retains binding activity. This has the advantage that the linkage is broken under mild conditions avoiding destruction of protein or other sensitive species present, and since the bonding between the antigen or hapten and its anti-antigen or anti-hapten binding partner is simply reversed, there is no problem with unwanted parts of the anti-antigen or anti-hapten remaining attached to the antigen or hapten binding partner or vice versa. This improvement in cleavage of the antigen/hapten linkage systems enables advantage to be taken of anti-antigen or anti-hapten specificity in isolating the desired entity in unmodified form from a complex mixture.

In particular, where one of the binding partners is a molecule on a cell surface, the cell can be bound, for example to a reporter substance or a solid support, and subsequently liberated with its reproductive potential undiminished.

According to the present invention, therefore, there is provided a method of cleaving an antigen/anti-antigen or hapten/anti-hapten linkage joining two particles comprising reacting said linkage with an secondary antibody, or fragment thereof, binding to said anti-antigen or anti-hapten.

The term "particles" as used herein means particulate bodies such as cells, sub-cellular components, polymer particles or other solid supports e.g. magnetic particles. While not wishing to be bound by theoretical explanations, it is possible that the action of the secondary antibody is assisted by strain on the affinity binding caused by relative movement of the two masses joined by the linkage to be broken. The linkage is thus destabilised, thereby facilitating detachment and preventing re-association. The secondary antibody may also act by binding to free antigenic sites unbound by the anti-antigen/anti-hapten thereby contributing to the destabilisation of the linkage.

In this specification, the terms anti-antigen and anti-hapten are intended to include complete anti-antigen or anti-hapten antibodies or any antigen or hapten binding fragments thereof, e.g. F(ab)2, Fab or Fv fragments (the Fv fragment is defined as the "variable" region of the antibody which comprises the antigen or hapten binding site.). The term "hapten" as used herein encompasses any small molecule which cannot by itself stimulate antibody synthesis but which will combine with an antibody formed by immunising an animal with an antigenic conjugate of the hapten and some antigenic substance, e.g. a protein such as keyhole limpet haemocyanin.

The secondary, linkage-cleaving, antibody directed against the anti-antigen or anti-hapten, (hereinafter referred to as the "secondary antibody") may be employed as the complete antibody, IgG and IgM antibodies being particularly preferred. Alternatively any fragments of the secondary antibody which retain binding activity may be used, for example F(ab)2, Fab or Fv fragments.

The secondary antibody is preferably directed against the Fab region of the anti-antigen or anti-hapten, but antibodies binding to any part of the anti-antigen or anti-hapten may be used. The secondary antibody may moreover be specifically directed against a particular part of the anti-antigen or anti-hapten molecule such as for example the kappa or lambda (K or π) light chains or even against a specific variable constant region within a given light chain.

Where the anti-hapten or anti-antigen has been used to attach a reporter substance or other species to the target hapten or antigen and the products cleaved from the target substance are water-soluble it may be advantageous for the secondary antibody (or fragment thereof) to be attached to particles, especially magnetic particles, to assist removal of the cleavage products from solution. Dynabeads (Dynal AS, Oslo) are particularly suitable for such use.

The secondary antibody may be mono- or polyclonal. The use of polyclonal sera has the advantage that since there are a number of different antibodies directed against different epitopes on the anti-antigen or anti-hapten, the binding of the secondary antibody or fragment, and thereby the efficacy of the method, is improved.

The new method of the invention may be used in the fields of analysis, diagnosis and cell isolation. For example, the method may be used in the isolation of infectious agents such as bacteria or viruses in order to quantitate them or characterise their infectivity, toxicity or susceptibility to drug treatment. The method can also be used for isolation of malignant cells or cell populations specific for different diseases and to characterise these cells further without interference from other contaminating cells. Also, the method may be used to isolate protective cell populations from an individual or from a group of individuals; the isolated population can then be expanded and/or potentiated before being returned to the patient under treatment. Such protective cell populations can for example be monocytes/macrophages, lymphocytes or bone marrow stem cells. As regards analytical applications, the method of the invention may be used in quantification and morphological analyses or in immunochemical staining studies employing both immunological and non-immunological markers.

As previously mentioned, the method of the invention is particularly suited to cell isolation, particularly in the possible selection of desirable cells using antibodies directed against the cells to be isolated (as opposed to negative selection procedures where unwanted cells are removed from a cell preparation using antibodies specific for the unwanted cells).

It has been proposed to positively isolate desired cells using magnetic beads coated with an antibody directed against a cell surface antigen, thus binding the desired cells, the magnetic particles and attached cells being separated from other cells by magnetic aggregation and the cells being liberated from the magnetic particles to leave a positively selected population of cells. In particular in PCT/EP90/02327 there is described such a method for the selection of haemopoietic stem cells from bone marrow and other mixed cell populations. In such methods, the magnetic particles are advantageously the superparamagnetic, monodisperse particles sold as Dynabeads (Dynal AS, Oslo).

Up to now, to liberate cells from the particles, the cell/particle "rosettes" have usually been incubated overnight at 37° C. to effect separation of the cells from the particles. In some cases the cells detach from the particles but in many cases they do not and such poor recovery makes difficult the isolation of poorly represented cell sub-populations. We have now found that the new method of the invention is particularly suited for detaching the bound cells from the magnetic particles.

According to a second aspect of the invention there is therefore provided a method of positively isolating a target cell type from a mixed population of cells wherein an anti-antigen is bound to an antigen on said target cell, said anti-antigen being attached to magnetic particles, before or after binding to said target cells, whereby to link said particles to said cells, the magnetic particles and attached cells are isolated from the mixed population of cells by magnetic aggregation and the target cell is released from said magnetic particle by the addition of an antibody, or fragment thereof, binding to said anti-antigen.

Although particularly suited to the isolation of haemopoietic stem cells, the method of the invention may be applied to the isolation of any prokaryotic or eukaryotic cells or viruses from biological or artificial media, including whole blood, buffy coat and cell suspensions obtained by density gradient centrifugation. Moreover it should be noted that the method according to the invention may be applied to the isolation and subsequent liberation of sub-cellular components such as mitochondria and nuclei, and macromolecules such as proteins and nucleic acids. The entity to be isolated may be naturally antigenic or may be made so artificially.

The amount of secondary antibody required for optimal cleavage will of course vary depending upon the entities bound, their ratio, and the number or quantity of entities eg. cells requiring isolation, and can readily be determined according to need. For example, in the case of positive cell selection mentioned above, the ratio of magnetic particles to target cells may vary in different systems and with different applications, and different amounts of the secondary antibody will accordingly be required to detach the cell from the particles.

Conditions for detachment may also be varied as appropriate. Thus rosetted cells, suspended in a suitable medium, may simply be incubated with the secondary antibody at ambient temperature. Alternatively the temperature may be reduced eg. to 4° C. or raised eg. to 37° C. Best results are obtained by incubating on an apparatus providing both gentle tilting and rotation.

When the method of the invention is to be used in the isolation of cells, the secondary antibody is normally obtained from a different species to that of the cells to be isolated. Mice, rats, sheep, swine and rabbits are all particularly suitable as sources of antibody. Thus for example in the isolation of human cells, the anti-antigen may conveniently be raised in mice, and the anti-immunoglobulin (Ig) antibody is an anti-mouse Ig (eg. as an anti-mouse-Fab) antibody raised in a different species such as sheep, goat or rabbits. Moreover if the cells to be isolated are human, it is advisable to remove all human Ig cross reactivity by passing the antibody/serum down a human-Ig column. In the case of a polyclonal secondary antibody preparation this may be obtained as the globulin fraction of serum following the ammonium sulphate precipitation.

The various reactants in the method of the invention are conveniently supplied in kit form. Thus in a third aspect, the present invention provides a kit comprising:

(i) a particulate solid support, preferably magnetic particles, carrying an anti-hapten or anti-antigen against a target antigen or hapten;

(ii) an antibody, or fragment thereof, binding with said anti-hapten or anti-antigen.

In a fourth aspect the invention provides a reagent comprising, for use in the method of the invention, an antibody or fragment thereof, binding with an anti-antigen or anti-hapten directed against a target antigen or hapten. The reagent according to the invention is conveniently supplied in lyophilised form, or as a sterile filtered buffered solution eg in 0.15 M phosphate buffered saline (PBS) at pH 7.4.

The invention will now be further described by way of the following non-limiting Example(s).

EXAMPLE 1

DETACHMENT OF BEADS FROM CELLS $5.10^6$ Daudi cells (Kvalheim G. et al, Bone Marrow Transplantation 1988; 3, 31–41) were incubated with $5.10^7$ Dynabeads M-450 Pan B (CD 19, Clone AB1, available from Dynal AS, Oslo, Norway) on a Rock-N-Roller (Lasenco, Lenco, Breda, the Netherlands) platform at 4° C. for 15 minutes to form rosettes. To detach the beads from the rosetted cells (in 0.5 ml RPMI (1% FBS)) 100 μl affinity purified goat anti-mouse-Fab (1.4 mg/ml) was added to the rosettes. The mixture was kept at 4° C. until the beads detached. For the described antigen/antibody system complete detachment occurred within 10–15 minutes leaving the cell with an intact antigen with no antibody bound. Similar results are obtained using sheep anti-mouse Fab or anti-mouse Fc.

EXAMPLES 2 TO 12

Following the protocol described in Example 1, successful detachment was observed in the following antigen/antibody systems. In Examples 2, 5, 6 and 7, antibody coated Dynabeads M-450 - CD4, CD8 or CD19 were obtained from Dynal AS. In the remaining Examples, the mouse monoclonal antibodies were coupled directly on to uncoated Dynabeads obtained from Dynal AS except Examples 10 and 11 where the antibodies were coupled to Dynabeads M-450 coated with sheep anti-mouse Ig. The antibodies used in the Examples are available from the following sources:

Examples 2 and 6:Dynal AS, Oslo, Norway
Examples 3, 5 and 12:Fred Hutchinson, Cancer Research Centre, Seattle, USA
Examples 4, 10 and 12:Biosys, France
Example 8:Institute of Molecular Genetics, Praha
Example 9:Serological Reagents Ltd., East-Grinstead, UK
Example 11:The Norwegian Radium Hospital, Oslo

| EXAMPLE | ANTIGEN/ANTIBODY | CELL |
|---|---|---|
| 2 | CD19/AB1 | Daudi cells |
| 3 | CD34/12,8 | KG 1a cells |
| 4 | CD34/B1-3C5 | KG 1a cells |
| 5 | CD4/66.1 | T Helper/inducer cells |
| 6 | CD8/5C2 | T suppressor/cytotoxic cell |
| 7 | CD19/AB1 | pan B cells |
| 8 | CD3/MEM.92 | pan T cells |
| 9 | CD10/RFAL3 | Lymphoid progenitor cells |
| 10 | CD13/MAS 392 P | Monocute, granulocyte |
| 11 | CD24/ML5/ML1/32D12 | B cells, granulocyte |
| 12 | CD34/12.8,/B1-3C5 | Haemopoietic precursor cell |

Example 13

T and B cells are detached using the following protocol:

1. Cells are positively isolated using antibody coated Dynabeads eg. Dynabeads M-450 CD4, CD8 or CD19, as recommended by the manufacturer (Dynal AS).
2. The rosetted cells are resuspended in tissue culture medium (eg. 100 μl of RPMI 1640/FCS).
3. Goat or sheep anti-mouse Ig is added to the rosetted cells.
4. The cells are incubated for 45–60 minutes at ambient temperature on an apparatus providing both gentle tilting and rotation. Care is taken that the cells remain in the bottom of the test tube during agitation.
5. The released beads are removed by placing the test tube in a magnetic particle concentrator (MPC from Dynal AS) for 2–3 minutes.
6. The cell suspension is pipetted from the test tube while the beads are attached to the wall of the tube by the MPC.
7. To obtain the residual cells, the detached beads are washed 2–3 times in culture medium (RPMI 1640/FCS or similar) and the supernatant is collected.
8. The detached cells are washed 2–3 times to remove the secondary antibody from the solution.
9. The cells are resuspended in an appropriate buffer.

The efficiency of detachment increases with the amount of secondary antibody applied.

Results obtained using the above protocol show that cells remain viable following detachment and antigen expression is unperturbed. Typical results are as follows:

Characterization of the Detached Cells

Purity: >99%
Viability: >98%

Antigen Expression of the Detached Cells

B cells: Unperturbed expression of CD5, CD19, CD20, CD21, CD23, CD24, CD37, CD40, CD45, CD75 and CD78. Expression of the CD69 activation antigen was not induced during the isolation/detachment procedure. The isolated cells could be transformed with Epstein Barr Virus (EBV).

T cells: Unperturbed expression of CD3, CD4 and CD8. More than 98% of the isolated cells express CD2. Expression of activation antigens such as CD25 (Tac), CD23, CD69 and 4F2 was not induced during the isolation/detachment procedure.

Activation Status of the Freshly Isolated Cells

>90% of the cells were in the Go (resting) phase as measured by cellular volume distribution, lack of expression of activation antigens and chromatin structure.

The isolated cells were stimulated in vitro using anti-μ heavy chain+B cell growth factor (low molecular weight BCGF) for B cells or anti-CD3+IL-2 for T cells. The following early and late activation parameters were demonstrated after stimulation:

Early Activation Parameters

Expression of activation antigens (CD69 on B cells, CD25 on T cells).
Volume increase.
Bulk RNA synthesis ($^3$H-uridine incorporation).

Late Activation Parameters

DNA synthesis ($^3$H-thymidine incorporation). Cell division (flow cytofluorometric cell cycle analysis).

Example 14

Antigen Preparation (a) Mouse Immunoglobulin

Serum from healthy, unimmunized Balb C mice was added to 1M NaCl, the pH was adjusted with 0.1 M NaOH to 8.5, the preparation was cooled to 4° C. and passed through a Sepharose-Protein A (Pharmacia) column adjusted to PBS/1 M NaCl, pH 8.5 at 4° C. After eluting the serum (10 ml) through the column (bed volume 15 ml) and washing with PBS/1 M NaCl, pH 8.5 at 4° C., the bound mouse IgG was eluted with 0.2 M acetate pH 4.0. This IgG was immediately neutralized with solid Tris concentrated with coilodium bags (Schleicher & Schuell UH 100/25 Ultrahulsen) and dialysed against PBS pH 7.3.

(b) Mouse Monoclonal IgG1 Fab and Fc Fragments

Ascites from Balb C mice growing hybridoma cell line 32D12 (IgG1) was added to 1 M NaCl concentration, the pH was adjusted with 0.1 M NaOH to 8.5, the preparation was cooled to 4° C. and passed through a Sepharose-Protein A (Pharmacia) column adjusted to PBS/1 M NaCl, pH 8.5 at 4° C. After eluting the ascites (5 ml) through the column (bed volume 15 ml) and washing with PBS/1 M NaCl, pH 8.5 at 4° C., the bound mouse IgG1 was eluted with 0.2 M acetate pH 4.0. This IgG was immediately neutralized with solid Tris concentrated with coilodium bags (Schleicher & Schuell UH 100/25 Ultrahulsen) and dialysed against PBS pH 7.3. A sample of the isolated IgG1 was digested (1:100 wt/wt) with papain (Sigma No P-3125) in the presence of 0.01 M DTT (Sigma No D-0632) and digested for I hour at 37° C. The digestion was stopped by adding iodoacetamide (Sigma No. I-6125) to 0.25 M concentration. After dialysis against PBS, the sample was added to 1 M NaCl concentration, the pH was adjusted to 8.5 and the temperature to 4° C. and passed through a Sepharose-Protein A (Pharmacia) column adjusted to PBS/1 M NaCl , pH 8.5 at 4° C. After eluting the sample through the column (bed volume 15 ml) the column was washed with PBS/1 M NaCl, pH 8.5 at 4° C. to elute the Fab fragments, and the bound mouse IgG1 Fc fragments were then eluted with 0.2 M acetate pH 4.0. These IgG1 Fab and Fc fragments were immediately neutralized with solid Tris concentrated with coilodium bags (Schleicher & Schuell UH 100/25 Ultrahulsen) and dialysed against PBS pH 7.3.

Preparation of Secondary Antibody 1. 50–250 μg antigen prepared according to (a) or (b) above in 0.5 ml phosphate buffered saline (PBS), pH 7.3 mixed with 0.75 ml Freund's Complete Adjuvant is administered to the sheep subcutaneously in several places on the back of the animal (50%) and intramuscularly in the thigh (50%).

2. After 2 weeks rest, this treatment is repeated.

3. After 2 weeks, this treatment is repeated once more.

4. After 2 weeks rest the animal is bled (about 500 ml whole untreated blood).

5. Bleeding is repeated each 2 weeks and if necessary a booster dose of antigen is given once a month.

6. The sheep is kept in production for about a year before it is terminated (or prolonged for about 6 months).

We claim:

1. A method of cleaving an antigen/anti-antigen or hapten/anti-hapten linkage joining two particles comprising binding to said anti-antigen or anti-hapten of said linkage a secondary antibody or antibody fragment that specifically binds to one or more sites in said anti-antigen or anti-hapten which are not the antigen-binding or hapten-binding sites and is effective upon binding Said one or more sites to cleave said linkage.

2. A method as claimed in claim 1 wherein the secondary antibody or antibody fragment binds to the Fab region of said anti-antigen or anti-hapten.

3. A method as claimed in claim 1 wherein the secondary antibody and/or anti-hapten or anti-antigen is a complete antibody.

4. A method as claimed in claim 1 wherein the anti-hapten or anti-antigen is an antibody fragment retaining binding activity.

5. A method as claimed in claim 1 wherein the secondary antibody or antibody fragment is an IgG or IgM.

6. A method as claimed in claim 1 wherein the secondary antibody or antibody fragment is polyclonal.

7. A method as claimed in claim 1 wherein in said linkage, the anti-antigen or anti-hapten is attached to a particulate solid support.

8. A method as claimed in claim 1 wherein the linkage joins an anti-antigen or anti-hapten carrying particulate solid support and surface-antigen or hapten carrying cells.

9. A method as claimed in claim 1 wherein the secondary antibody is attached to particles.

10. A method of positively isolating target cells from a mixed population of cells comprising binding an anti-antigen attached to magnetic particles to antigen on said target cells, said anti-antigen being attached to magnetic particles before or after binding to said target cells, thereby binding said particles to said target cells, isolating said magnetic particles and bound target cells from the mixed population of cells by magnetic aggregation, releasing the target cells from said magnetic particles by adding under conditions effective for binding to occur a secondary antibody or antibody fragment that specifically binds to one or more sites in said anti-antigen which are not the antigen-binding sites and that is effective upon binding said one or more sites to cleave the binding between said target cells and said anti-antigen, thereby isolating the released target cells from said mixed population.

11. A method as claimed in claim 10 wherein the secondary antibody or antibody fragment is from a different species from that of the target cell.

12. A kit comprising:
   (i) a particulate solid support carrying an anti-antigen or anti-hapten specific for a target antigen or hapten;
   (ii) a secondary antibody or antibody fragment that specifically binds to one Or more sites in said anti-antigen or anti-hapten which are not the antigen-binding or hapten-binding sites and is effective upon binding said one or more sites to cleave the antigen/anti-antigen or hapten/anti-hapten linkage formed upon binding of said antigen to Said anti-antigen or Said hapten to said anti-hapten.

13. A kit as claimed in claim 12 wherein the solid support comprises magnetic particles.

* * * * *